| United States Patent [19] | [11] Patent Number: 5,030,749 |
| Hussmann | [45] Date of Patent: Jul. 9, 1991 |

[54] METHOD FOR PRODUCING PURIFIED TRIMESIC ACID

[75] Inventor: Gregory P. Hussmann, Warrenville, Ill.

[73] Assignee: Amoco Corporation, Chicago, Ill.

[21] Appl. No.: 805,113

[22] Filed: Dec. 4, 1985

[51] Int. Cl.$^5$ .................. C07C 51/265; C07C 51/43
[52] U.S. Cl. .................... 562/414; 562/416
[58] Field of Search .................. 562/414, 416

[56] References Cited

U.S. PATENT DOCUMENTS

| 3,115,520 | 12/1963 | Baldwin et al. | 562/414 |
| 3,119,860 | 1/1964 | Kalfadelis et al. | 562/414 |
| 3,171,856 | 3/1965 | Kurtz | 562/414 |
| 3,210,416 | 10/1965 | Fragen | 562/514 |
| 3,261,846 | 7/1966 | Meyer | 562/414 |
| 3,354,202 | 11/1967 | Zimmerschied | 562/414 |
| 3,859,344 | 1/1975 | Shigeyasu et al. | 562/414 |
| 3,928,433 | 12/1975 | Onopchenko | 562/414 |
| 4,051,178 | 9/1977 | Kimura et al. | 562/416 |

*Primary Examiner*—Vivian Garner
*Attorney, Agent, or Firm*—James R. Henes; William H. Magidson; Ralph C. Medhurst

[57] ABSTRACT

A method is disclosed for producing purified trimesic acid prepared by a process involving the liquid-phase oxidation of mesitylene in a solvent consisting of an aliphatic $C_2$–$C_6$ monocarboxylic acid, water or a mixture thereof in the presence of an oxidation catalyst comprising cobalt, manganese and bromine components, crystallizing crude trimesic acid by cooling to about 80° C. to about 150° C., separating crystallized trimesic acid from the mother liquor at a temperature in the range of 80° C. to about 105° C. and washing the separated crude trimesic acid crystals with water at a temperature of from about 10° C. to about 100° C.

10 Claims, No Drawings

METHOD FOR PRODUCING PURIFIED TRIMESIC ACID

BACKGROUND OF THE INVENTION

1. Field of the Invention

This invention relates generally to a method for producing trimesic acid by the liquid-phase oxidation of mesitylene in a solvent, and more particularly concerns a method for producing purified trimesic acid by a process involving the aforesaid liquid-phase oxidation.

2. Discussion of the Prior Art

Trimesic acid is employed as a monomer in the production of specialty polymers and resins. Trimesic acid is also employed in the preparation of germicides, fungicides, plasticizers and cross-linking agents. Obviously, the presence of impurities in trimesic acid can have a serious adverse effect on the physical or chemical properties or performance characteristics of any formulation containing trimesic acid itself or any polymer formed from trimesic acid. In addition, impurities in trimesic acid can adversely affect polymerization processes to which the trimesic acid is subjected. Such impurities in trimesic acid formed by the catalyzed, liquid-phase oxidation of mesitylene are often organic impurities or byproducts formed during the oxidation and inorganic impurities corresponding to metal components of the catalysts employed in the oxidation or formed therefrom.

Thus, removal of such impurities from trimesic acid is highly desirable. However, the removal of organic and inorganic impurities from aromatic polycarboxylic acids formed by the catalyzed, liquid-phase oxidation of polyalkyl aromatics is typically very difficult, and the removal technique employed depends on the specific aromatic polycarboxylic acid from which the impurities are to be removed and the specific oxidation conditions and catalyst employed to make it.

For example, terephthalic acid and naphthal-ene-2,6-dicarboxylic acid are purified by entirely different techniques. Purified terephthalic acid is conventionally derived from relatively less pure, technical grade or "crude" terephthalic acid formed by the liquid-phase oxidation of p-xylene in an acetic acid-water solvent in the presence of a catalyst comprising cobalt-, manganese-, and bromine-containing components by purification of the latter utilizing hydrogen and a noble metal catalyst as described in U.S. Pat. No. 3,584,039 to Meyer. In the purification process, the impure terephthalic acid is dissolved in water at an elevated temperature, and the resulting solution is hydrogenated, preferably in the presence of a hydrogenation catalyst, e.g., palladium on a carbon support, as described in U.S. Pat. No. 3,726,915 to Pohlmann. This hydrogenation step converts the various color bodies present in the relatively impure terephthalic acid to colorless products. Another related purification-by-hydrogenation process for aromatic polycarboxylic acids produced by liquid-phase catalyst oxidation of polyalkyl aromatic hydrocarbons is described in U.S. Pat. No. 4,405,809 to Stech et al. By contrast, formation of the methyl ester is the best method known for purifying naphthal-ene-2,6-dicarboxylic acid formed by the liquid-phase oxidation of 2,6-dimethylnaphthalene in an acetic acid-water solvent in the presence of a catalyst comprising cobalt-, manganese-, and bromine-containing components. However, both aforesaid techniques for purifying terephthalic acid and naphthylene-2,6-dicarboxylic acid are relatively time consuming and involve relatively complex reaction schemes.

OBJECTS OF THE INVENTION

It is therefore a general object of the present invention to provide an improved method which overcomes the aforesaid problem of prior art methods for purifying crude trimesic acid produced by the liquid-phase oxidation of mesitylene with an oxygen-containing gas in a solvent and in the presence of an oxidation catalyst comprising cobalt-, manganese-, and bromine-containing components.

More particularly, it is an object of the present invention to provide a fast and simple method for purifying crude trimesic acid produced by the aforesaid liquid-phase oxidation of mesitylene which affords a trimesic acid product having reduced contents of organic and inorganic impurities and is easier to dry.

Other objects and advantages of the invention will become apparent upon reading the following detailed description and appended claims.

SUMMARY OF THE INVENTION

These objects are achieved by the method of this invention for producing purified trimesic acid comprising: oxidizing mesitylene with an oxygen-containing gas in the liquid phase in a solvent at an elevated temperature and pressure and in the presence of an oxidation catalyst comprising cobalt, manganese, and bromine components to form a product mixture comprising crude trimesic acid; crystallizing the crude trimesic acid by cooling the product mixture to a temperature in the range of from about 80° C. to about 105° C.; separating the crystallized trimesic acid from the product mixture at a temperature in the range of from about 80° C. to about 105° C.; and washing the separated crude trimesic acid with water at a temperature in the range of from about 10° C. to about 100° C. and at a weight ratio of water-to-separated trimesic acid in the range of from about 0.5:1 to about 10:1 to form purified trimesic acid.

DETAILED DESCRIPTION OF THE PREFERRED EMBODIMENTS

Suitable solvents for use in the oxidation step of the method of this invention include any aliphatic $C_2$-$C_6$ monocarboxylic acid such as acetic acid, propionic acid, n-butyric acid, isobutyric acid, n-valeric acid, trimethylacetic acid, and caproic acid and water and mixtures thereof. Preferably, the solvent is a mixture of acetic acid and water, which more preferably contains from 1 to 20 weight percent of water, as introduced into the oxidation reactor. Since heat generated in the highly exothermic liquid-phase oxidation is dissipated at least partially by vaporization of solvent in the oxidation reactor, some of the solvent is withdrawn from the reactor as a vapor, which is then condensed and recycled to the reactor.

The source of molecular oxygen employed in the oxidation step of the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the gas-vapor mixture in the condenser.

The catalyst employed in the oxidation step of the method of this invention comprises cobalt, manganese, and bromine components, and can additionally comprise accelerators known in the art. Preferably, the catalyst consists essentially of the cobalt-, manganese-, and bromine-containing components. The weight ratio of cobalt (calculated as elemental cobalt) in the cobalt component of the catalyst-to-mesitylene in the liquid-phase oxidation is in the range of from about 0.1 to about 10 milligram atoms (mga) per gram mole of polyalkyl aromatic. The weight ratio of manganese (calculated as elemental manganese) in the manganese component of the catalyst-to-cobalt (calculated as elemental cobalt) in the cobalt component of the catalyst in the liquid-phase oxidation is in the range of from about 0.1 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.1 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromine can be employed. The 0.1:1.0 to 1.5:1.0 bromine-to-total cobalt and manganese milligram atom ratio is provided by a suitable source of bromine. Such bromine sources include elemental bromine ($Br_2$), or ionic bromide (e.g., HBr, NaBr, KBr, $NH_4Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of 0.1:1.0 to 1.5:1.0. The bromine ion released from the organic bromides at the oxidation operating conditions can be readily determined by known analytical means. Tetrabromoethane, for example, at operating temperatures of 170° C. to 225° C. has been found to yield about 3 effective gram atoms of bromine per gram mole.

In operation, the minimum pressure at which the oxidation reactor is maintained is that pressure which will maintain a substantial liquid phase of the mesitylene and at least 70 percent of the solvent. The mesitylene and solvent not in the liquid phase because of vaporization are removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 kg/cm² to about 35 kg/cm², and typically are in the range of from about 10 kg/cm² to about 30 kg/cm². the temperature range within the oxidation reactor is generally from about 120° C., preferably from about 150° C., to about 240° C., preferably to about 230° C. The solvent residence time in the oxidation reactor is generally from about 20 to about 150 minutes and preferably from about 30 to about 120 minutes.

The oxidation can be performed either on a continuous or semicontinuous basis. In the continuous mode, each of the mesitylene, air, solvent, and catalyst are continuously introduced into the reactor, and a product stream comprising trimesic acid and catalyst components dissolved in the solvent is withdrawn from the reactor. In the semicontinuous mode, the solvent and catalyst are initially introduced into the reactor and then mesitylene and air are continuously introduced into the reactor.

Thereafter, the product stream in the continuous mode or the reactor contents in the semicontinuous mode are cooled to a temperature in the range of from about 80° C. to about 105° C. in at least one step and in at least one crystallizer such that essentially all of the trimesic acid crystallizes in the solvent. Following crystallization, the resulting slurry of trimesic acid in the mother liquor is separated, typically by centrifugation, at a temperature in the range of from about 80° C. to about 105° C. Generally the separation is performed at essentially the same temperature as the crystallization.

The benefits of the aforesaid temperature range for both the crystallization and separation of trimesic acid in the method of this invention are illustrated by the results in Table 1 of analyses of trimesic acid samples produced using the same oxidation conditions, which conditions are within the ranges therefor described hereinabove. The samples analyzed had been washed with acetic acid after being separated.

The organic impurities tested in Table 1 constitute at least 80 weight percent of the total organic impurities in trimesic acid produced in accordance with the oxidation conditions of the method of this invention. The optical densities reported herein were obtained by measurement of the absorbance of a 2 weight percent solution of trimesic acid in aqueous ammonium hydroxide at a frequency of 320 nanometers.

The results in Table 1, illustrate clearly that a trimesic acid product having substantially lower levels of organic impurities and improved optical density is obtained when the trimesic acid is crystallized and filtered at a temperature in the range of from about 80° C. to about 105° C.

As illustrated hereinabove in Table 1, even if the crystallization and separation are performed under the conditions therefor of the method of this invention, after separation of the mother liquor, the resulting trimesic acid contains undesirable inorganic and organic impurities. However, I have found that the concentrations in trimesic acid of both organic and inorganic impurities, but particularly of the inorganic metal impurities, are reduced substantially by washing the filter cake with water. Although a water wash is ineffective in removing either organic or inorganic impurities from terephthalic acid and naphthalene-2,6-dicarboxylic acid, a water wash is very effective in removing organic and inorganic impurities from trimesic acid and, in fact, as indicated by the data in Table 2 hereinbelow, is much more effective than an acetic acid wash in the removal of organic and inorganic impurities from trimesic acid and in improving the color characteristics of trimesic acid.

TABLE 1

| Impurities | Concentration (parts per million by weight) in Trimesic Acid Crystallized and Separated at | |
|---|---|---|
| | 24° C. | 104° C. |
| cobalt | 132 | 117 |
| manganese | 376 | 389 |
| bromine | 158 | 125 |
| trimellitic anhydride | 107 | 85 |
| terephthalic acid | 429 | 73 |
| isophthalic acid | 2525 | 1002 |
| benzoic acid | 987 | 911 |
| 5-methylisophthalic acid | 4001 | 911 |
| tetracarboxybenzene | 1482 | 1289 |
| dicarboxybenzaldehyde | 356 | 146 |
| Properties | | |
| acid number | 778 | 789 |
| optical density | 1.93 | 1.39 |

TABLE 2

| | Concentration[1] in Trimesic Acid[2] | | | |
|---|---|---|---|---|
| | Without Wash[3] | Acetic Acid Wash[4] | Water Wash A[5] | Water Wash B[6] |
| Impurity | | | | |
| trimellitic anhydride | 205 | 46 | 31 | 37 |
| terephthalic acid | 176 | 94 | 60 | 66 |
| isophthalic acid | 1633 | 475 | 386 | 400 |
| 5-methylisophthalic acid | 1407 | 609 | 321 | 338 |
| 3,5-dimethylbenzoic acid | 78 | 38 | 34 | 39 |
| cobalt | 290 | 268 | 22 | 35 |
| manganese | 442 | 357 | 50 | 51 |
| bromine | 207 | 97 | 81 | 78 |
| Properties | | | | |
| optical density | 1.33 | 0.71 | 0.68 | 0.68 |
| color | pink | pink | white | white |

Footnotes:
[1] Parts per million by weight
[2] Obtained by crystallization and separation, each at 93° C.
[3] Typical values for trimesic acid prepared under similar oxidation conditions and then crystallized and separated at 90° C.
[4] At 93° C. with 1 part of acetic acid per 1 part of filter cake by weight
[5] At 66° C. with 1 part of water per 1 part of filter cake by weight
[6] At 10° C. with 1.2 parts of water per 1 part of filter cake by weight The washed samples of trimesic acid were prepared in the same oxidation run and using oxidation conditions within the ranges therefor described hereinabove. The organic impurities listed in Table 2 constitute at least 80 weight percent of the total organic impurities in trimesic acid produced in accordance with the oxidation conditions of the method of this invention.

The water wash step of the method of this invention is performed at a temperature in the range of from about 10° C., preferably from about 25° C., to about 100° C., preferably to about 50° C., and a weight ratio of water-to-trimesic acid filter cake in the range of from about 0.5:1, preferably from about 1:1, to about 10:1, preferably to about 1.5:1. The water wash is performed for a time in the range of from about 0.5 minute to about 5 minutes.

The resulting purified trimesic acid contains less than 0.5 %, preferably less than 0.1%, of total organic impurities and less than 0.05%, preferably less than 0.02% of total inorganic impurities, based on the weight of the trimesic acid.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

1. A method for producing purified trimesic acid comprising: oxidizing mesitylene with an oxygen-containing gas in the liquid phase in a solvent consisting essentially of an aliphatic a $C_2$–$C_6$ monocarboxylic acid, water or a mixture thereof, at an elevated temperature and pressure and in the presence of an oxidation catalyst comprising cobalt, manganese, and bromine components to form crude trimesic acid in the solvent; crystallizing the crude trimesic acid by cooling the crude trimesic acid to a temperature in the range of from about 80° C. to about 105° C.; separating the crystallized trimesic acid from the mother liquor at a temperature in the range of from about 80° C. to about 105° C.; and washing the separated crude trimesic acid with water at a temperature in the range of from about 10° C. to about 100° C. and at a weight ratio of water to separated trimesic acid in the range of from about 0.5:1 to about 10:1 form purified trimesic acid.

2. The method of claim 1 wherein the solvent in the oxidation step is a mixture of acetic acid and water containing from 1 to 20 weight percent of water in the reactor.

3. The method of claim 1 wherein the oxidation step is performed at a temperature in the range of from about 120° C. to about 240° C.

4. The method of claim 1 wherein the oxidation step is performed at a gauge pressure in the range of from about 10 to 30 kg/cm$^2$.

5. The method of claim 1 wherein the weight ratio of cobalt (calculated as elemental cobalt) in the cobalt component of the catalyst-to-mesitylene in the liquid phase oxidation is in the range of from about 0.1 to about 10 mga per gram mole of mesitylene, the weight ratio of manganese (calculated as elemental manganese) in the manganese component of the catalyst-to-cobalt (calculated as elemental cobalt), in the cobalt component of the catalyst is in the range of from about 0.1 to about 10 mga per mga of cobalt, and the weight ratio of bromine (calculated as elemental bromine) in the bromine component of the catalyst-to-total cobalt and manganese (calculated as elemental cobalt and elemental manganese) in the cobalt and manganese components of the catalyst is in the range of from about 0.1 to about 1.5 mga per mga of total cobalt and manganese.

6. The method of claim 1 wherein air is the oxygen-containing gas.

7. The method of claim 1 wherein the separated crude trimesic acid is washed with water at a temperature in the range of from about 25° C. to about 50° C.

8. The method of claim 1 wherein the separated crude trimesic acid is washed with water at a weight ratio of water to separated trimesic acid in the range of from about 1:1 to about 1.5:1.

9. The method of claim 1 wherein the purified trimesic acid contains less than 0.1 percent of total organic impurities, based on the weight of trimesic acid.

10. The method of claim 1 wherein the purified trimesic acid contains less than 0.02 percent of total inorganic impurities, based on the weight of trimesic acid.

* * * * *

UNITED STATES PATENT OFFICE
CERTIFICATE OF CORRECTION

Patent No. 5,030,749     Dated  July 9, 1991

Inventor(s)  Gregory P. Hussmann

It is certified that error appears in the above-identified patent and that said Letters Patent is hereby corrected as shown below:

| Col. | Line | |
|---|---|---|
| 1 | 39 | "naphthal-ene-2,6-" should read --naphthalene-2,6- -- |
| 1 | 62 | "naphthal-ene-2,6-" should read --naphthalene-2,6-- |
| 3 | 10 | "bro-mine-containing" should read --bromine-containing-- |
| 4 | 21 | "separated, typicallY" should read --separated, typically-- |
| 6 | 36 | "catalyst*to*mesitylene" should read --catalyst to mesitylene-- |

Signed and Sealed this

Thirteenth Day of October, 1992

Attest:

DOUGLAS B. COMER

Attesting Officer    Acting Commissioner of Patents and Trademarks